United States Patent
Chan et al.

(10) Patent No.: US 11,300,261 B2
(45) Date of Patent: Apr. 12, 2022

(54) LED CANDLE LIGHT

(71) Applicant: Aurora International Limited, Hong Kong (HK)

(72) Inventors: Chiko Jeckle Chan, Hong Kong (HK); Joe Deleo, Hong Kong (HK); Shuaisi Ye, Hong Kong (HK)

(73) Assignee: Aurora International Limited, Hong Kong (HK)

( * ) Notice: Subject to any disclaimer, the term of this patent is extended or adjusted under 35 U.S.C. 154(b) by 0 days.

(21) Appl. No.: 17/321,495

(22) Filed: May 16, 2021

(65) Prior Publication Data

US 2021/0270435 A1 Sep. 2, 2021

Related U.S. Application Data

(63) Continuation of application No. PCT/CN2020/078746, filed on Mar. 11, 2020.

(30) Foreign Application Priority Data

Jul. 3, 2019 (CN) .......................... 201921027974.3

(51) Int. Cl.
*F21S 10/04* (2006.01)
*F21S 9/02* (2006.01)
(Continued)

(52) U.S. Cl.
CPC ............... *F21S 10/043* (2013.01); *F21S 9/02* (2013.01); *F21S 10/046* (2013.01); *F21V 23/04* (2013.01);
(Continued)

(58) Field of Classification Search
CPC ........ F21S 10/04; F21S 10/043; F21S 10/046; A61L 2209/12; A61L 2209/133; A61L 9/037
See application file for complete search history.

(56) References Cited

U.S. PATENT DOCUMENTS

| 4,829,495 A * | 5/1989 | Kaneko | G04B 17/02 |
|---|---|---|---|
| | | | 368/134 |
| 9,585,980 B1 * | 3/2017 | Li | F21S 6/001 |
| 9,664,348 B1 * | 5/2017 | Chen | F21S 6/001 |

(Continued)

FOREIGN PATENT DOCUMENTS

| CN | 107035992 A | 8/2017 |
|---|---|---|
| CN | 109578924 A | 4/2019 |
| CN | 110630947 A | 12/2019 |

OTHER PUBLICATIONS

International Search Report of PCT Patent Application No. PCT/CN2020/078746 dated May 27, 2020.

*Primary Examiner* — Rajarshi Chakraborty
*Assistant Examiner* — Michael Chiang

(57) ABSTRACT

An LED candle light includes an outer housing, a battery pack provided at an inner bottom portion of the outer housing and controlled by a power control board, a coil provided above the battery pack, a mounting frame fixed in the outer housing, an LED light fixed on the mounting frame, the LED light being electrically connected with the battery pack, a flame cover covering an outer periphery of the LED light, a pendulum connected with a lower portion of the flame cover through a rotating shaft, and a magnet provided at a bottom portion of the pendulum, the magnet being located directly above the coil. The present disclosure can simulate a candle and is energy-saving, environmentally friendly, greatly amusing, highly ornamental, safe and harmless.

8 Claims, 8 Drawing Sheets

(51) Int. Cl.
 *F21V 23/04* (2006.01)
 *F21Y 115/10* (2016.01)
 *F21S 6/00* (2006.01)

(52) U.S. Cl.
 CPC .......... *A61L 2209/12* (2013.01); *F21S 6/001* (2013.01); *F21Y 2115/10* (2016.08)

(56) References Cited

U.S. PATENT DOCUMENTS

| | | | | |
|---|---|---|---|---|
| 2010/0207502 | A1* | 8/2010 | Cao | F21V 29/51 313/46 |
| 2014/0211499 | A1* | 7/2014 | Fong | F21S 9/02 362/558 |
| 2014/0362592 | A1* | 12/2014 | Lee | F21L 4/08 362/386 |
| 2016/0146414 | A1* | 5/2016 | Dong | F21S 6/001 362/232 |
| 2017/0122512 | A1* | 5/2017 | Yuan | F21S 10/04 |
| 2018/0103507 | A1* | 4/2018 | Davis | H05B 1/0244 |
| 2018/0340678 | A1* | 11/2018 | Pan | F21S 10/046 |
| 2019/0145593 | A1* | 5/2019 | Huang | F21V 23/06 362/569 |
| 2019/0195447 | A1* | 6/2019 | Wu | B05B 1/14 |
| 2020/0217469 | A1* | 7/2020 | Fan | F21S 6/001 |

* cited by examiner

LED CANDLE LIGHT

CROSS REFERENCE TO RELATED APPLICATIONS

The present application is a Continuation Application of PCT Application No. PCT/CN2020/078746 filed on Mar. 11, 2020, which claims the benefit of Chinese Patent Application No. 201921027974.3 filed on Jul. 3, 2019. All the above are hereby incorporated by reference in their entirety.

TECHNICAL FIELD

The present disclosure relates to the field of lighting, in particular to an LED candle light which is energy-saving, environmentally friendly, greatly amusing, highly ornamental, safe and harmless.

BACKGROUND TECHNOLOGY

Candle light is a kind of light bulb. It is named because its shape is similar to that of a candle flame. The light is soft, yellow and has the feeling of a candle flame. Therefore, it is loved by more and more users. However, existing candle light cannot simulate the effect of a swinging flame when a candle is burning, nor can it imitate the lighting manner of flickering and dimming of a burning candle. Therefore, its degree of simulation is low. It is not quite amusing, and thus cannot satisfy the increasing demand and usage requirement of people.

SUMMARY

In order to overcome the shortcomings of the prior art, the purpose of the present disclosure is to provide an LED candle light that is energy-saving, environmentally friendly, greatly amusing, highly ornamental, safe and harmless.

The present disclosure is realized through the following technical solutions. An LED candle light may include an outer housing, a battery pack provided at an inner bottom portion of the outer housing and controlled by a power control board, a coil disposed above the battery pack, a mounting frame fixed in the outer housing, an LED light fixed on the mounting frame, the LED light being electrically connected with the battery pack, a flame cover covering an outer periphery of the LED light, a pendulum connected with a lower portion of the flame cover through a rotating shaft, and a magnet provided at a bottom portion of the pendulum, the magnet being located directly above the coil.

As a preferred manner, the flame cover is a silicone cover that allows light to pass therethrough.

As a preferred manner, a bottom portion of the mounting frame is provided with a hanging hook, and a weight of the pendulum is provided with a hanging ring. The hanging ring is hanged on and connected to the hanging hook. The supporting frames on both sides of the pendulum are connected with the rotating shaft, so that when the pendulum swings, the flame cover is driven to swing.

As a preferred manner, a metal plate, having a recessed central portion and a bent edge, is provided around a lower portion of the flame cover. The recessed portion of the metal plate may be provided with water or aromatic essential oil.

As a preferred manner, a bottom portion of the metal plate is provided with a thermistor, and the thermistor is electrically connected with the battery pack.

As a preferred manner, the metal plate is an aluminum plate.

As a preferred manner, one or a plurality of the LED lights is provided, and the plurality of the LED lights are disposed at different angles with respect to the mounting frame.

As a preferred manner, a surface of the outer housing is provided with a switch, and the switch is electrically connected with the battery pack.

The battery pack of the present disclosure provides direct current of unregulated voltage output to the LED light under the control of the power control board, so that the LED light emits flickering light. When the battery pack provides direct current of unregulated voltage output to the coil, an irregular magnetic field is generated after the coil is energized. The magnetic force of the magnetic field repels the magnet, causing the pendulum to move irregularly in directions away from the electromagnetic coil, thereby driving the flame cover to swing irregularly. Hence, it can simulate irregular swinging of a flame when a candle is burning. The flickering effect is more amusing, safer and more environmentally friendly.

DETAILED DESCRIPTION OF EMBODIMENTS

Figure 1:
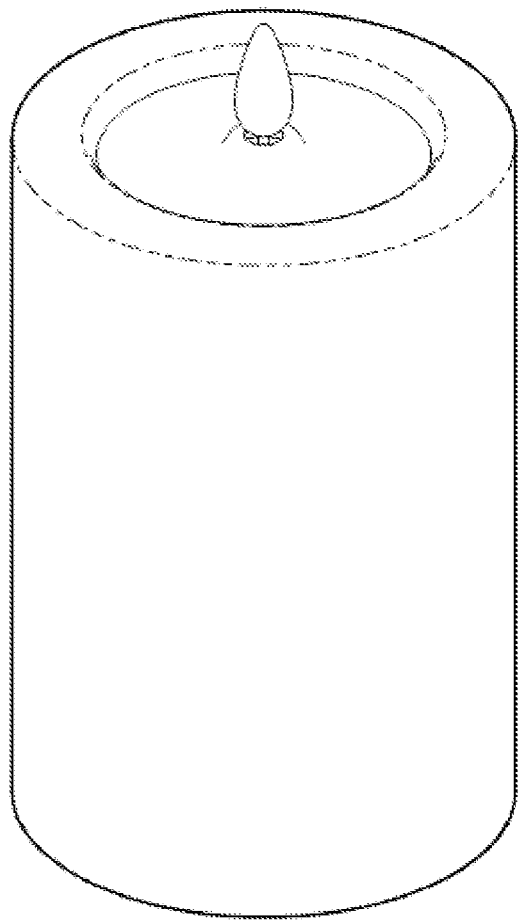
FIG. 1 is a schematic diagram of the overall structure of an embodiment of the present disclosure.
Figure 2:
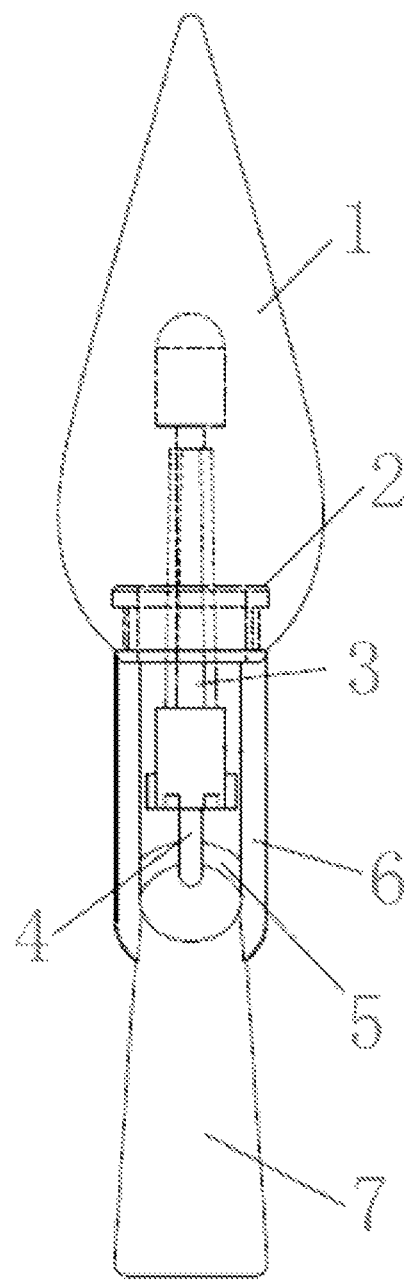
FIG. 2 is a schematic diagram of the internal structure of an embodiment of the present disclosure.

The present disclosure will be further described below in detail in conjunction with the embodiments and the accompanying drawings.

Referring to FIGS. 1-8, an LED candle light includes an outer housing, a battery pack 10 provided at an inner bottom portion of the outer housing and controlled by a power control board 11, a coil 9 provided above the battery pack 10, a mounting frame 3 fixed in the outer housing, an LED light 8 fixed on the mounting frame 3, the LED light 8 being electrically connected with the battery pack 10, a flame cover 1 covering an outer periphery of the LED light 8, a pendulum 7 connected with a lower portion of the flame cover 1 through a rotating shaft 2, and a magnet provided at a bottom portion of the pendulum 7, the magnet being located directly above the coil 9.

The battery pack 10 of the LED candle light is under the control of the power control board 11 to provide the LED light 8 with direct current of unregulated voltage output, so that the LED light 8 can emit flickering light. When the battery pack 10 provides the coil 9 with direct current of unregulated voltage output, an irregular magnetic field is generated after the coil 9 is energized. The magnetic force of the magnetic field repels the magnet, causing the pendulum 7 to move irregularly in directions away from the electromagnetic coil, and thereby driving the flame cover to swing irregularly. Hence, it can simulate irregular swinging of a flame when a candle is burning. The flickering effect is more amusing, safer and more environmentally friendly. It can enhance the market competitiveness of the product.

Figure 3:
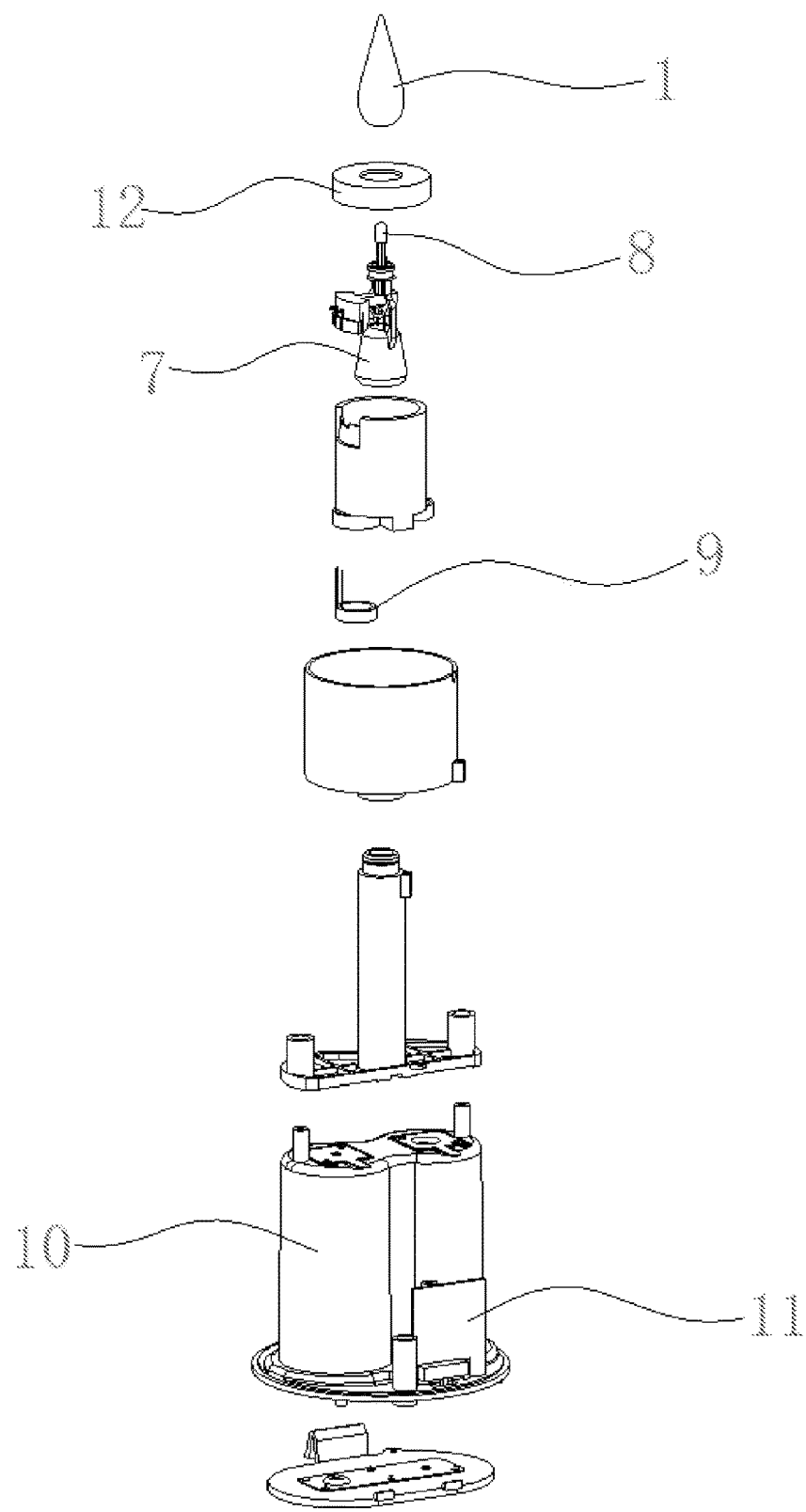
FIG. 3 is an exploded view of the internal structure of an embodiment of the present disclosure.

Referring to FIG. 3, in an embodiment of the LED candle light, the flame cover 1 can be a silicone cover that allows light to pass therethrough. As a result, the light passing through is more uniform, and the emitted light is softer. This is beneficial in the protection of eyesight.

Figure 4:
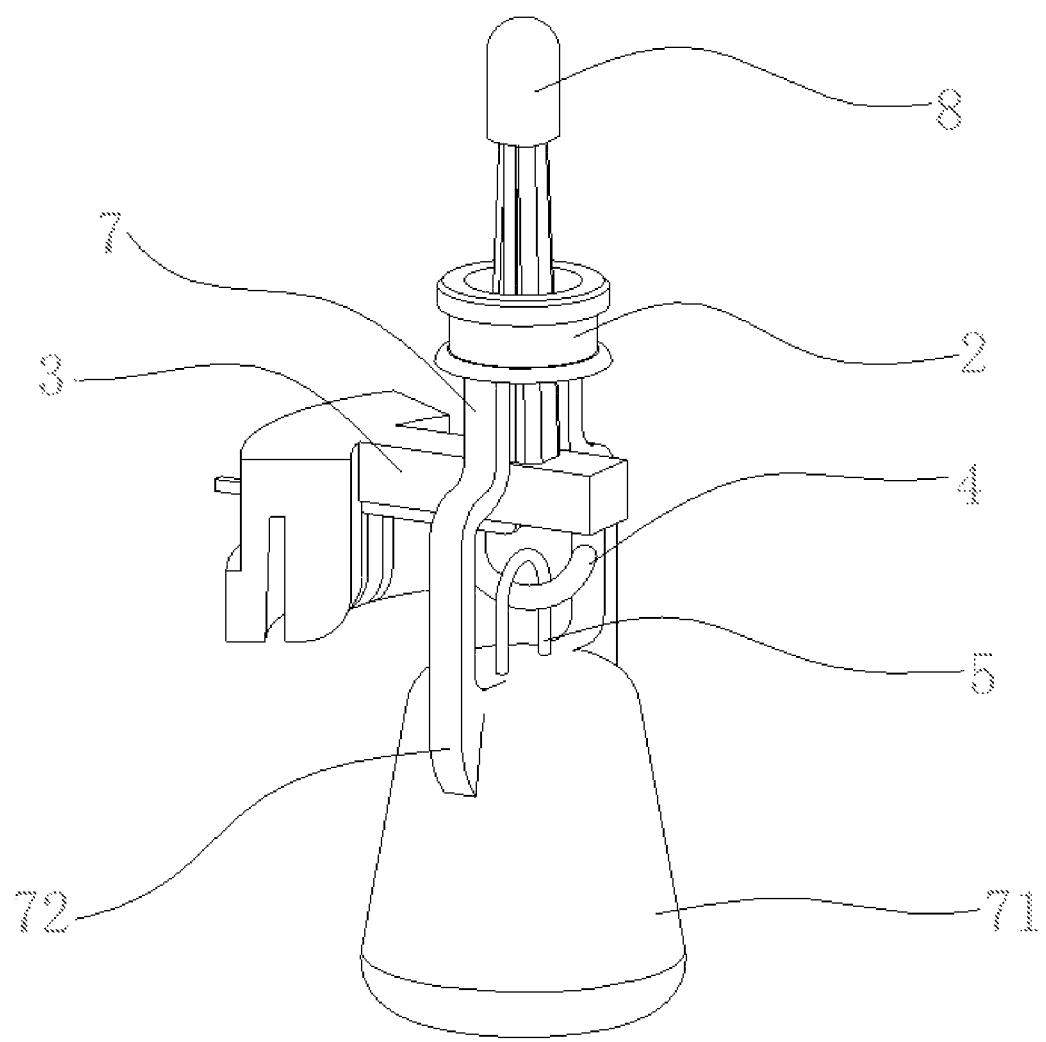
FIG. 4 is a schematic diagram of the pendulum-rotating shaft linkage structure of an embodiment of the present disclosure.
Figure 5:
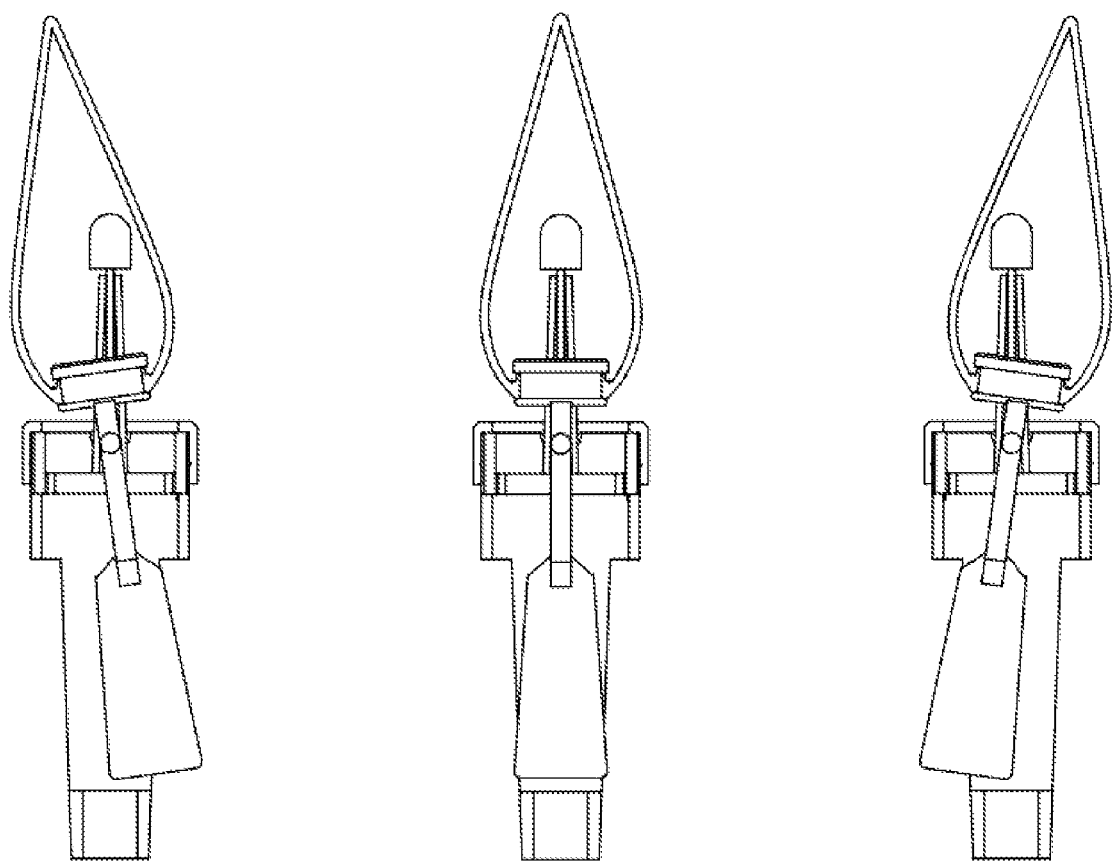
FIG. 5 are schematic diagrams of the swinging states of the pendulum of an embodiment of the present disclosure.

Referring to FIG. 4, in an embodiment of the LED candle light, a bottom portion of the mounting frame 3 is provided with a hanging hook 4. A weight 71 of the pendulum 7 is provided with a hanging ring 5. The hanging ring 5 is hanged on and connected to the hanging hook 4. Supporting frames 72 on both sides of the pendulum 7 are connected with the rotating shaft 2, so that when the pendulum 7 swings, the flame cover 1 is driven to swing.

Referring to FIG. 3, a specific embodiment of the LED candle light based on the above technical solution may include a metal plate 12 having a recessed central portion and a bent edge. The metal plate 12 may be provided around the lower portion of the flame cover 1. A bottom portion of the metal plate 12 is provided with a thermistor, and the thermistor is electrically connected with the battery pack 10. Hence, when the battery pack 10 provides direct current to the thermistor, the thermistor can heat the metal plate 12 with low power so that the temperature of the metal plate 12 is a few degrees higher than room temperature. When water or aromatic essential oil is added to the recess of the metal plate 12, it can slowly evaporate the water or aromatic essential oil to achieve moisturizing or fragrance effect.

Referring to FIG. 3, in a specific embodiment of the LED candle light based on the above technical solution, the metal plate 12 may be an aluminum plate. As a result, it is lighter in weight, and the weight of the product can be reduced.

Figure 6:
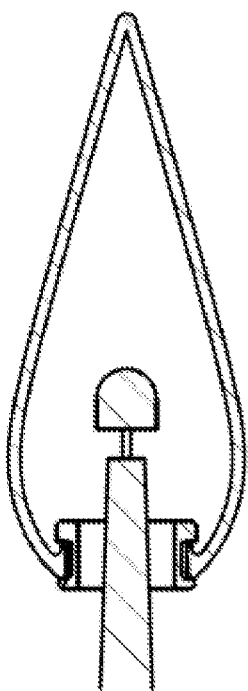
FIGS. 6 to 8 are schematic diagrams of the setting of the LED lights of the embodiments of the present disclosure.
Figure 7:
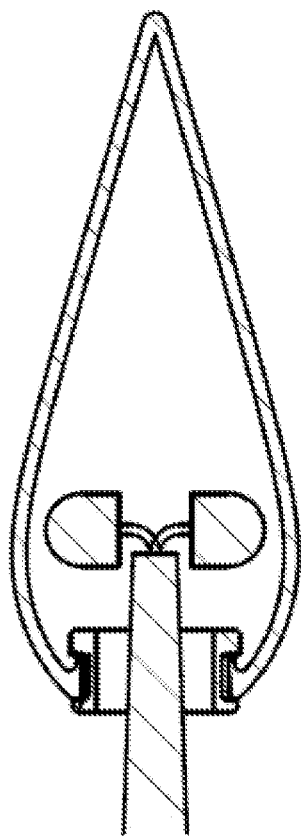
Figure 8:
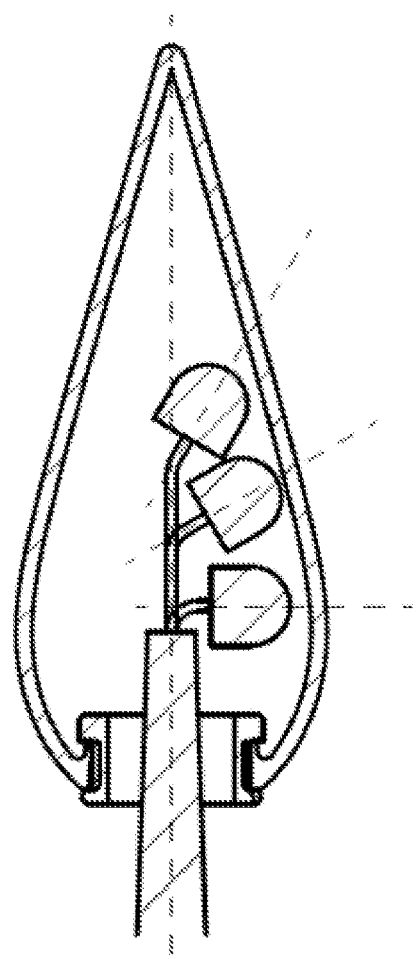

Referring to FIGS. 6-8, in a specific embodiment of the LED candle light based on the above technical solution, a plurality of the LED lights 8 may be provided. The plurality of the LED lights 8 can be disposed at different angles with respect to the mounting frame 3. Hence, a candle with different "flames" is generated, and it is greatly amusing. Of course, the LED lights 8 can also have different colors so that it can satisfy the requirement of lighting of different colors.

Referring to FIG. 1, in a specific embodiment of the LED candle light based on the above technical solution, a switch may be provided on a surface of the outer housing, and the switch is electrically connected to the battery pack 10. Therefore, it is convenient to control the turn-on and turn-off of the LED candle light.

The above is an explanation of the LED candle light to help the understanding of the present disclosure, but the implementation of the present disclosure is not limited by the above-mentioned embodiments. Any changes, modifications, substitutions, combinations, and simplifications made without departing from the principle of the present disclosure should all be equivalent replacements, and they are all included in the scope of protection of the present disclosure.

What is claimed is:

1. An LED candle light, comprising an outer housing, a battery pack provided at an inner bottom portion of the outer housing and controlled by a power control board, a coil provided above the battery pack, a mounting frame fixed in the outer housing, an LED light fixed on the mounting frame, the LED light being electrically connected with the battery pack, a flame cover covering an outer periphery of the LED light, a pendulum connected with a lower portion of the flame cover through a rotating shaft, a magnet provided at a bottom portion of the pendulum, the magnet being located directly above the coil, and a weight of the pendulum hanged on and connected to the mounting frame through a hanging hook and a hanging ring, so that when the pendulum swings, the flame cover is driven to swing.

2. The LED candle light according to claim 1, wherein the flame cover is a silicone cover that allows light to pass therethrough.

3. The LED candle light according to claim 1, wherein a bottom portion of the mounting frame is provided with the hanging hook, the weight of the pendulum is provided with the hanging ring, the hanging ring is hanged on and connected to the hanging hook, and supporting frames on both sides of the pendulum are connected with the rotating shaft.

4. The LED candle light according to claim 1, wherein a metal plate, having a recessed central portion and a bent edge, is provided around the lower portion of the flame cover.

5. The LED candle light according to claim 4, wherein a bottom portion of the metal plate is provided with a thermistor, and the thermistor is electrically connected with the battery pack.

6. The LED candle light according to claim 5, the metal plate is an aluminum plate.

7. The LED candle light according to claim 1, wherein a plurality of the LED lights is provided, and the plurality of the LED lights are disposed at different angles with respect to the mounting frame.

8. The LED candle light according to claim 1, wherein a surface of the outer housing is provided with a switch, and the switch is electrically connected with the battery pack.

* * * * *